United States Patent [19]

Yamamoto

[11] Patent Number: 4,847,049

[45] Date of Patent: Jul. 11, 1989

[54] METHOD OF FORMING CHELATED COLLAGEN HAVING BACTERICIDAL PROPERTIES

[75] Inventor: Ronald Yamamoto, Redwood City, Calif.

[73] Assignee: Vitaphore Corporation, Menlo Park, Calif.

[21] Appl. No.: 28,645

[22] Filed: Mar. 20, 1987

Related U.S. Application Data

[63] Continuation-in-part of Ser. No. 811,171, Dec. 18, 1985, abandoned.

[51] Int. Cl.$^4$ .......................... C08H 1/06; C08L 89/04; C08L 89/06
[52] U.S. Cl. ...................................... 422/24; 106/125; 204/157.68; 430/642; 530/356
[58] Field of Search ................. 530/356; 106/125; 204/157.68; 422/24; 430/642

[56] References Cited

U.S. PATENT DOCUMENTS

| | | | |
|---|---|---|---|
| 2,304,478 | 10/1939 | Rosenzweig | 8/128 |
| 3,152,976 | 10/1964 | Kuntz | 204/157.68 |
| 3,380,848 | 4/1968 | Horowitz | 424/78 X |
| 3,427,301 | 2/1969 | Needles et al. | 530/356 X |
| 3,748,142 | 7/1973 | Battista | 430/642 |
| 3,792,161 | 11/1970 | Fox, Jr. | 424/94 |
| 3,800,792 | 4/1974 | McKnight et al. | 128/156 |
| 4,280,954 | 7/1981 | Yannas et al. | 530/356 |
| 4,294,241 | 10/1981 | Miyata | 128/156 |
| 4,424,188 | 1/1984 | Di Geronimo | 422/24 X |
| 4,446,124 | 5/1984 | Fox, Jr. et al. | 424/95 X |
| 4,448,718 | 5/1984 | Yannas et al. | 530/356 |
| 4,451,397 | 5/1984 | Huc et al. | 530/356 |
| 4,488,911 | 12/1984 | Luck et al. | 204/157.68 |
| 4,505,855 | 3/1985 | Bruns et al. | 204/157.68 |
| 4,581,028 | 4/1986 | Fox, Jr. et al. | 424/95 X |

FOREIGN PATENT DOCUMENTS

| | | |
|---|---|---|
| 099758 | 2/1984 | European Pat. Off. . |
| 1588933 | 4/1981 | United Kingdom . |
| 2138302 | 10/1984 | United Kingdom . |

OTHER PUBLICATIONS

Light–Sensitive Systems: pp. 16–21, 54–63 and 187, Kosar, published 1965.
Fox et al., *Ann. Chir. Plast.*, 24(3), 25–267.

*Primary Examiner*—Howard E. Schain
*Attorney, Agent, or Firm*—Flehr, Hohbach, Test, Albritton & Herbert

[57] ABSTRACT

A method is provided for protecting renatured collagen against bacterial and fungal attack by contacting the collagen with a silver ion-containing solution at a pH from 4.0 to 9.0 and exposing the silver-chelated collagen to ultraviolet radiation.

8 Claims, 2 Drawing Sheets

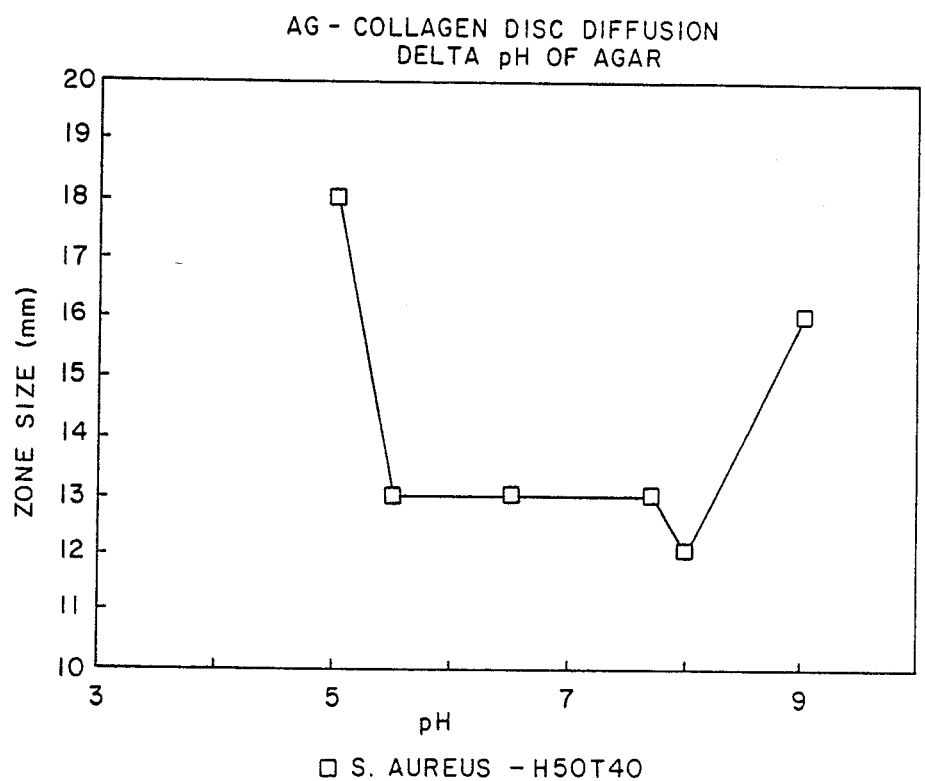
FIG. — 3

METHOD OF FORMING CHELATED COLLAGEN HAVING BACTERICIDAL PROPERTIES

This is a continuation-in-part of Ser. No. 811,171 filed Dec. 18, 1985, now abandoned.

The present invention is directed to a method of producing silver-chelated collagen. In particular, the present invention provides a method for forming silver-chelated collagen for use in medical devices and therapeutic compositions.

BACKGROUND OF THE INVENTION

Inherent in the use of medical devices, particularly in the use of devices which are at least in partial contact with body fluids, is the problem of infection. Furthermore, therapeutic uses of collagen, particularly for wound healing, repair of scar tissue, and cosmetic surgery, is becoming increasingly important. The problem with collagen, as with any other substance which is foreign to the body, is how to make these proteinaceous substances substantially sterile and/or inhibitive to infection. The present invention provides a method for producing antibacterial and antifungal collagen for such uses.

The type of collagen to which the present invention is applicable is insoluble, renatured collagen in the form of felts, foams, sponges, and films which are porous. By the term renatured, it is meant that the collagen is not collagen in its natural state, but rather it has been denatured to its triple helix form (often called tropocollagen or procollagen) by treatment of natural collagen with salt solutions, acid solutions and/or denaturing enzymes, then reprecipitated into collagen fibril. The fibrils are held together by bonding forces between the side chains of the amino acid residues of the protein chains, the main bond being hydrogen bonds. The association of fibrils into macromolecules, again by primarily hydrogen bonding, renatures, or reconstitutes, the collagen. The advantage of a renatured collagen is that, particularly in the case when denaturing enzymes are used, the renatured collagen is of much higher purity, being stripped of telopeptides and/or saccharides, thus resulting in collagen which is less antigenic than the naturally-occurring collagen. As used herein, the term renatured collagen also includes collagen which has been reconstituted to reform hydrogen bonding and chemically cross linked using chemical cross linking reagents such as, dialdehydes, diesters, diamines, and the like.

While treatment of some types of collagen with silver nitrate or other silver salts is known in the art (see Fox, et al., *Ann. Chir. Plast.*, Vol. 24 (No. 3) pp. 265–267 (1979); and U.S. Pat. No. 4,294,241), it is believed that it has not been heretofore shown to improve collagen by forming a reconstituted and/or cross linked collagen having improved silver ion retention by treatment of ultraviolet radiation.

It is thus an object of the present invention to provide improved collagen having antibacterial and antifungal properties.

It is yet another object of the present invention to provide medical devices containing collagen on at least one surface thereof which has improved bactericidal and fungicidal properties.

It is yet another object of the present invention to provide topical therapeutic agents comprising collagen having improved antibacterial and antifungal properties.

Other objects and advantages of the present invention will be apparent from a further reading of the following specification and appended claims.

SUMMARY OF THE INVENTION

The present invention provides a method for protecting insoluble renatured collagen against bacterial and fungal attack comprising the steps of contacting the renatured collagen with silver ion-containing solution at a pH in the range from 4.0 to 9.0 to cause silver ions to be chelated to functional groups in the renatured collagen; and exposing the silver-chelated collagen to ultraviolet radiation of sufficient energy for a sufficient period of time to strengthen the binding of the silver ions to the renatured collagen without substantial formation of metallic silver or other oxidation products of silver (I).

In one preferred embodiment, the silver-chelating functional groups on the renatured collagen are increased by modifying the collagen by chemical means. The amino acid side chains in the collagen may be guanidated, modified by reaction with N-carboxy-amino acid anhydrides, or reacted with chondroiten sulfate. These modifying agents add additional sites for silver chelation, thereby enhancing the capacity of the collagen to retain silver.

BRIEF DESCRIPTION OF THE DRAWINGS

In the accompanying drawings:

FIG. 3 is a plot of results of a Kirby-Bauer test against *S. aureus*.

DESCRIPTION OF THE INVENTION

Figure 1:
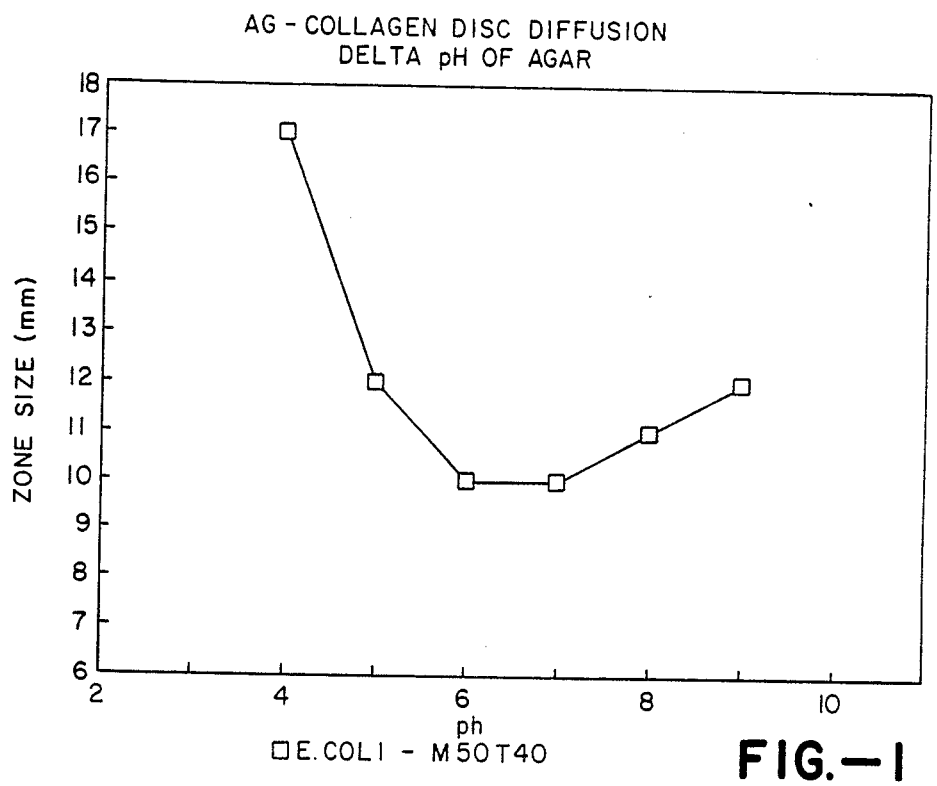
FIG. 1 is a plot of the size of the bactericidal zone versus pH in a Kirby-Bauer test of a composition according to the invention against *E. coli*.

While exposure of natural collagen or gelatin to ultraviolet radiation in the presence of a photosensitive inorganic reagent, such as dichromate, hardens the gelatin or collagen by oxidation, this also consumes the dichromate, which is reduced. See Kosar, J. *Light-Sensitive Systems*, Wiley & Sons, New York, pp. 54–55 (1965); and U.S. Pat. No. 3,745,011 to Hudgin. While silver salts may also be utilized as photoinitiators in this way, the silver ion would also be consumed by a similar reaction by oxidation of functional chains in the proteins. However, according to the present invention, the consumption of the silver ion by oxidation upon exposure to ultraviolet light is to be avoided, since the object of exposure to ultraviolet light is not to oxidize and cross link the protein with a corresponding reduction of the silver ion, but rather to conserve the silver ion as a silver ion chelate for slow release into the environment, thus protecting the renatured collagen from fungal and bacterial attack for a prolonged period of time.

It has thus been surprisingly found that the exposure of a renatured collagen, and particularly, exposure of a covalently cross-linked renatured collagen, to ultraviolet radiation results in strengthening of the binding forces of the chelated silver ions to the collagen without substantial formation of metallic silver or other reduction products of silver (I).

A particularly advantageous result of the practice of the present invention is the increase of the silver binding capacity of the renatured collagen. As an example, in a typical renatured collagen sponge, the silver ion binding is increased up to about 50% when the silver ion is bound using the ultraviolet radiation according to the present invention. A typical result is the enhancement of the silver binding from 36.6 mg silver per gram collagen to 20.7 mg silver per gram collagen. Another particularly advantageous feature of the present invention is the increase of the period of time over which the silver retained in the collagen. When exposed to an aqueous environment, collagen impregnated with silver ion would leach the silver almost as rapidly as the salt is solubilized, therefore the rate of solubilization would be directly proportional to the degree to which the silver ion is bound to the collagen. In a typical example, in a stirred aqueous environment at pH 6 at 37° C., an ultraviolet-treated silver-collagen sponge made in accordance with the present invention loses 41.6% of its silver into the solution after 3 hours.

By comparison a similar silver-collagen sponge not treated with ultraviolet radiation loses 50.3% of its silver into the solution over that period of time.

A third particularly advantageous feature of the present invention is the relatively slow release of the silver ions into the aqueous environment. This is an advantage since too rapid a release of silver ions, which might occur if the silver ions were not tightly bound to the collagen, would also tend to irritate the surrounding tissues. Utilizing the silver-collagen made in accordance with the present invention, tissue irritation is thus minimized.

The collagen may be renatured to its insoluble form from natural sources such as bovine corium (hide), bovine tendon, and porcine skin. Preprocessed, insoluble collagen from animal sources is also commercially available as hemostatic agents under trade names such as Collastat ™, Gelfoam ™ sponge and Avitene ™ nonwoven web. Methods of forming renatured collagen are known in the literature, including, for example, as described in U.S. Pat. Nos. 4,294,241 and 3,823,212.

A particularly preferred form of renatured collagen for utilization in accordance with the present invention is one which has been renatured and covalently cross-linked. This collagen may be prepared by utilizing readily available polyfunctional cross linking agents, such as dialdehydes, dicarboxylic acids, diamines, and the like. A typical procedure involves dissolving tropocollagen in a buffer of pH 3.0 to 5.0 wherein the solution contains approximately 1 to 2% by weight of the collagen. Then 1% of a dialdehyde cross-linking agent such as glutaraldehyde or formaldehyde is then added and the mixture frozen and stored for approximately 24 hours. After thawing and washing to remove unreacted cross linking agent, the renatured cross-linked collagen will be ready for contact with the silver ion-containing solution.

The source of silver ion may be a water soluble silver salt, preferably silver nitrate. While the concentration of the silver ion in the solution is not particularly critical, it will be usually convenient to utilize solutions in the concentration range of about 10 to $10^3$ millimolar.

The renatured collagen will be contacted with a silver ion-containing solution in the pH range of about 4 to 9. The pH of the silver ion-containing solution will be controlled by the addition of an appropriate titrating agent, such as nitric acid, or potassium hydroxide, as required, to maintain the pH at less than about 9.0 to avoid the degradation of the silver. There is not believed to be any lower limit for the pH, however, normally a pH above 4.0 will be convenient. A particularly preferred range for the pH is from 7.0 to 7.5. The binding capacity of silver by collagen is particularly effective within this preferred pH range, although the amount of binding by silver by the collagen is further controllable by the concentration of the silver ion-containing solution and/or exposure time of the collagen to the silver ion-containing solution. Simultaneous with or subsequent to exposure of the collagen to the silver ion-containing solution, the collagen is then exposed to ultraviolet radiation of energy and duration sufficient to strengthen the binding of the silver ions to the collagen without substantial formation of metallic silver formed as a result of oxidation of various functional groups in the collagen by the silver ion. While the exact limits of the ranges of the conditions which will be sufficient to strengthen the binding of the silver ions without substantial formation of metallic silver are not precisely determinable, it will generally suffice to maintain the pH of the silver-collagen environment at less than 8.0 while exposing the collagen to ultraviolet radiation in the range of about 210 to 310 nm wavelength for about from 5 to 15 minutes. The time of UV exposure for complete reaction is inversely proportional to the light intensity which is preferably in the range of 100 to 1,000 microwatts/cm$^2$. A slight coloration of the collagen due to the exposure to ultraviolet radiation is acceptable, i.e., a turning from white to a light brown to yellow color, indicating a slight oxidation reaction occurring in the collagen, however the radiation should not be to the extent that dark brown or black areas in the collagen occur due to overoxidation and/or substantial formation of metallic silver. Normally the exposure will be performed at ambient temperatures, i.e., in the range of about 20° to 25° C., however, there is not believed to be any reason why the exposure could not occur at higher or lower temperatures providing that the temperature is not high enough to cause degradation of the collagen and/or silver ion. There is not believed to be any lower limit to the temperature at which the exposure may take place, provided it is above the freezing point of the ion-containing solution.

Ultraviolet radiation may be provided by any conventional ultraviolet radiation source of appropriate wavelength, such as germicidal lamps and mercury/xenon lamps.

The renatured collagen prepared in accordance with the present invention is particularly useful in the preparation of medical devices to be used in contact with bodily fluids and tissues. Thus, such devices as sutures, wound dressings, and tissue ingrowth implant coatings which may contain collagen to assist in the healing process, may be made from the collagen provided in accordance with the present invention.

Other uses of the renatured collagen according to the present invention include uses in topical therapeutic compositions which contain collagen, such as collagen which is used in cosmetic surgery.

In another particularly preferred embodiment of the present invention, the number of functional groups in the collagen which are chelatable to silver ions is enhanced by reacting modifying agents which add functional groups with the collagen. While not intending to be bound by any particular theory, it is believed that the silver ion is primarily chelated in the collagen to amine groups, either from the free amino ends of the peptides or, primarily, from the nitrogen-containing side chains of the amino acids, lysine, hydroxylysine, asparagine, glutamine and arginine. This is suggested by an assay of free amines utilizing ortho-phthaldehyde fluorescence (by the technique described by Bensen, et al., *Proc. Nat. Acad. Sci.*, Vol. 72 (No. 2), pp. 619–622 (1975)) of a renatured collagen versus a silver-chelated renatured collagen in accordance with the present invention which shows 86.9% reduction in ortho-phthaldehyde reactivity, indicating a corresponding reduction in the number of available amine groups due to chelation with the silver ions.

Thus, one method of enhancing the number of silver chelatable groups in the collagen is to guanidate the collagen utilizing known protein guanidation techniques. Guanidation converts the side chain of lysine residues into arginine residues which have twice the amine content, thus increasing silver binding capacity. Guanidation may be readily performed upon collagen, for example, by soaking in a 0.2 to 1 molar solution of o-methylisourea at a pH in the range of 10.2 to 11. Another method of guanidation is to treat the renatured collagen with GDMP (1-guanyl-3,5-dimethylpyrazole nitrate) at a concentration of 0.5 to 0.2 M at a pH of 9.5. It has been found that guanidation of renatured collagen increases the silver binding capacity by approximately 200 to 400%.

There are several other chelatable groups within the amino acids in collagen, such as the carboxyl groups of aspartate and glutamate. However, carboxyl groups in general do not bind as tightly to silver ions as amine groups. The sulfhydryl groups on the side chains of methionine and cysteine also tightly bind silver ions, although their occurrence in most collagen protein chains is less than that of amine groups. Due to the differences among the energies of chelation of silver ion with amine, carboxyl and sulfhydryl groups, the silver binding capacity and release characteristics of the particular collagen may be modified to meet desired medical applications. This may be done by adding amino acids to the collagen by use of activated amino acids such as N-carboxy-alpha amino acid anhydrides (NCAs) onto free amino groups on the protein chains within the collagen to form amide bonds. Thus treatment of the renatured collagen with arginine NCA would create additional amine binding sites, whereas treatment with cysteine would add sulfhydryl binding sites. Treatment of a collagen with aspartate or glutamate NCA would add carboxyl sites which have a lower chelation binding energy with silver than amines or sulfhydryl groups. By selection of the particular type of NCAs, the overall binding capacity and release characteristics of the collagen may be modified as desired, depending on the particular end use of the collagen.

A third method of modifying the collagen is to treat the collagen with chondroiten sulfate, a natural tissue proteoglycan found predominantly in cartilage. Chondroiten sulfate has a repeating disaccharide structure with ester sulfate groups pendent from the carbohydrate ring. The number of ester sulfates varies, with an average of about 0.8 sulfate groups per disaccharide. The binding of the chondroiten sulfate to the collagen is ionic in nature and may be accomplished by soaking the collagen in an aqueous solution of chondroiten sulfate of a concentration preferably in the range of 10 to 200 mg/ml at a pH of 2.5 to 4.5 for about 1 hour. The collagen is then washed and then soaked in an appropriate silver ion-containing solution whereby the ester sulfate groups, which chelate the silver ions, increase the total silver binding capacity of the collagen. A typical treatment may increase the silver binding capacity of a renatured collagen by 50%.

A particular use, as discussed above, for the collagen prepared according to the present invention, is as a medical device for contact with bodily fluids and tissues. The particularly preferred device for that application is a positionable tissue interfacing device for the management of percutaneous conduits, which is generally described for example, in commonly assigned U.S. Ser. No. 653,442 filed Sept. 21, 1984. The collagen components of such devices will comprise the tissue ingrowth material allowing the formation of a tissue seal without the risk of bacterial proliferation in the porous matrix.

Another use for the collagen in accordance with the present invention is as a wound healing and scar tissue concealing material for cosmetic surgery. Uses of collagen in this manner are per se known, however, the utilization of the collagen made according to the present invention reduces the chance and occurrence of infection at the wound and scar site.

Having described the preferred embodiments of the present invention, the following example is given to further illustrate the present invention. The scope of the invention is not to be limited by the specific details of the example.

EXAMPLE

A solution of 500 mls. of demineralized water containing 8.5 grams of silver nitrate is titrated to a pH between 7 to 7.5. To this solution 20 grams of collagen (commercially available from Sigma Chemical Co.) are placed while maintaining a temperature at 25° C. Mixing is continued for approximately 30 minutes. Also during this period of time, ultraviolet radiation from a mercury lamp is used to expose the solution.

The collagen is collected by filtration, washed and tested for bactericidal activity by the Kirby-Bauer swabbed plate method. Referring to the FIGURES, the results show the bactericidal activity as detected by this test on three plate transfers.

Figure 2:
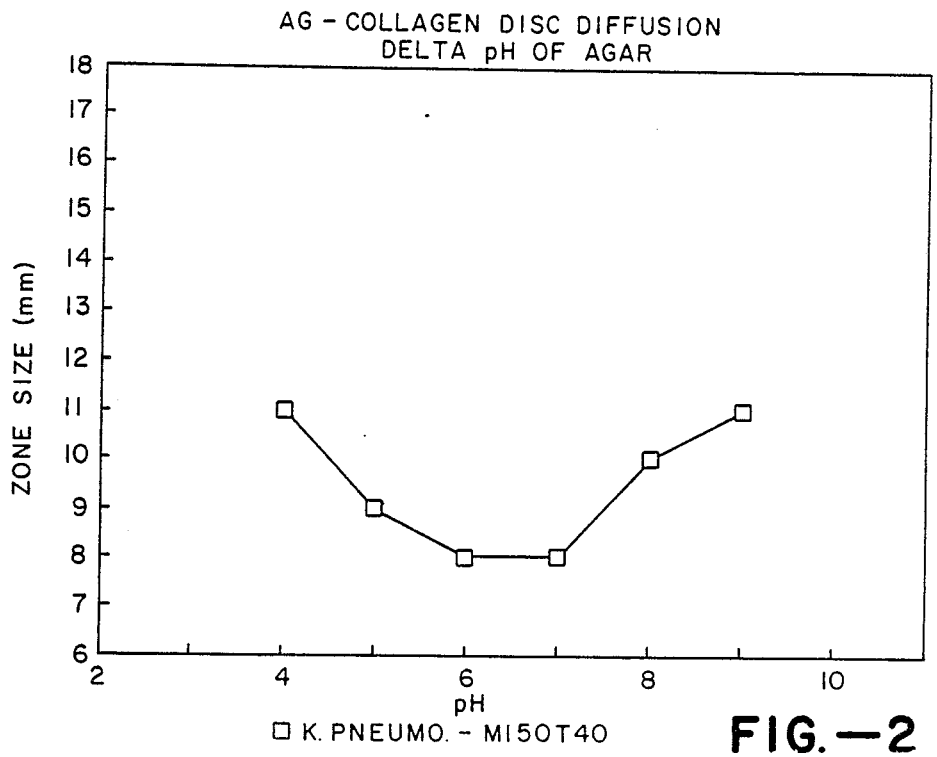
FIG. 2 is a plot of results of a Kirby-Bauer test against *K. pneumo*.

Referring to FIG. 1, there is shown a plot of the diameter of the zone size exhibiting antibacterial activity against *E. coli* versus the pH of the Mueller-Hinton test medium used to swab a plate in the Kirby-Bauer test. The zone size increased (i.e., antibacterial activity increased) as pH increased or decreased from about pH 6.0–7.0. FIG. 2 is a plot of the same parameters in a test against *K. pneumo*. FIG. 3 is a plot of the same parameters in a test against *S. aureus*. These three microorganisms are commonly associated with clinical infections. The effect of enhancement of bactericidal activity with increasing acidity or basicity of the medium is advantageous, since the pH at a wound site will usually decrease as infection is resisted by local tissue defenses.

What is claimed is:
1. A method for protecting collagen against bacterial and fungal attach comprising the step of exposing renatured, water insoluble, covalently cross-linked collagen in the presence of an aqueous silver ion-containing solution a a pH in the range of from 4.0 to 9.0 to ultraviole radiation of suffcent energy and for a period of time sufficent to bind a non-toxic amount of said silver ions to said collagen without substantial formation of metallic silver or silver oxide.

2. A method according to claim 1 wherein said pH is in the range of 7.0 to 7.5.

3. A method according to claim 1 wherein said collagen comprises renatured collagen modified to increase silver-chelating functional groups.

4. A method according to claim 3 wherein said modified collagen is guanidated.

5. A method according to claim 3 wherein said collagen is modified by reaction with N-carboxy-alpha-amino acid anhydrides selected from the group consisting of N-carboxy-cysteine-anhydride, N-hydroxy-arginine anydride, N-carboxy-aspartic acid anhydride and N-carboxy-glutamic acid anhydride.

6. A method according to claim 3 wherein said collagen is modified by reaction with chondroiten sulfate.

7. An infection resistant medical device for contact with bodily fluids or tissues characterized by a bodily-fluid contacting surface comprising renatured, water insoluble, covalently cross-linked collagen, said collagen being bound to a non-toxic amount of silver ions by exposure of said collagen in the presence of a silver-ion containing solution at a pH in the range of from 4.0 to 9.0 to ultraviolet radiation of sufficient strength and for a period of time sufficient to bind said non-toxic amount of silver ions to said collagen without substantial formation of metallic silver or silver oxide.

8. A topical therapeutic agent comprising renatured, water insoluble, covalently cross-linked collagen complexed with a non-toxic amount of silver ions, said collagen formed by exposing renatured, water insoluble covalently cross-linked collagen with a silver ion-containing solution at a pH in the range of 4.0 to 9.0 to ultraviolet radiation of sufficient duration and for a period of time sufficient to bind said non-toxic amount of silver ions to said collagen without substantial formation of metallic silver or silver oxide.

* * * * *